United States Patent [19]

James

[11] Patent Number: 5,456,105
[45] Date of Patent: Oct. 10, 1995

[54] RHEOMETER FOR DETERMINING EXTENSIONAL ELASTICITY

[75] Inventor: David F. James, Toronto, Canada

[73] Assignee: International Paper Company, Purchase, N.Y.

[21] Appl. No.: 136,354

[22] Filed: Oct. 14, 1993

[51] Int. Cl.$^6$ .......................... G01N 11/00; G01N 11/04
[52] U.S. Cl. ........................ 73/54.01; 73/54.13; 73/54.31
[58] Field of Search ............................ 73/54.13, 54.14, 73/54.11, 54.01, 54.31

[56] References Cited

U.S. PATENT DOCUMENTS

| | | | |
|---|---|---|---|
| 1,427,922 | 9/1922 | Tiffany | 73/54.17 |
| 2,431,378 | 4/1944 | Eitzen et al. | 73/54.15 |
| 2,780,096 | 2/1957 | Noble et al. | 73/54.13 X |
| 3,242,720 | 3/1966 | Zavasnik | 73/54.13 |
| 3,512,239 | 5/1970 | Okamoto | 73/54.21 |
| 3,758,776 | 9/1973 | Frohne et al. | 73/54.14 |
| 4,185,493 | 1/1980 | Feinstein | 73/54.13 |
| 4,313,339 | 2/1982 | Nichols et al. | 73/54.14 |
| 4,517,830 | 5/1985 | Gunn et al. | 73/54.15 |
| 4,612,799 | 9/1986 | Choi et al. | 73/54.36 |
| 4,680,958 | 7/1987 | Ruelle et al. | 73/54.14 |
| 5,209,107 | 5/1993 | Grudzien, Jr. et al. | 73/54.14 |

FOREIGN PATENT DOCUMENTS

| | | |
|---|---|---|
| 933172 | 9/1955 | Germany . |
| 148267 | 6/1962 | U.S.S.R. ............... 73/54.13 |
| 751958 | 7/1956 | United Kingdom . |

OTHER PUBLICATIONS

Wazer et al., "Viscosity and Flow Measurement", 1963; Interscience Publishers, pp. 244–247.
Lyne, M. B., The Importance of Extensional Viscosity in the Impression of Ink Into Paper During Printing, 1989, pp. 236–248.
Pangalos, G. et al., Rheological Properties of News Inks, 1985, The Journal of Rheology, vol. 29(4), pp. 471–491.
James, David F. et al., Extensional Flow of Dilute Polymer Solutions, J. Fluid Mech., 1980, vol. 97, part 4, pp. 655–672.
James, D. F. et al., A Converging Channel Rheometer for the Measurement of Extensional Viscosity, Journal of Non–Newtonian Fluid Mechanics, 35, 1990, pp. 421–443.
James, David F. et al., Flow of Dilute Polymer Solutions Through Converging Channels, Journal of Non–Newtonian Fluid Mechanics, 11, 1982, pp. 317–339.

Primary Examiner—Hezron E. Williams
Assistant Examiner—Michael J. Brock
Attorney, Agent, or Firm—Ostrager, Chong & Flaherty

[57] ABSTRACT

A method determining the extensional elasticity of a fluid includes the step of determining the shear viscosity of a fluid in a flow field where the shear rate of the fluid is substantially uniform. A valve indicative of the shear viscosity and extensional elasticity is obtained by performing measurements in a flow field where a portion of the body of the fluid is accelerated. The two values are then compared to obtain an indicator of the extensional elasticity.

6 Claims, 2 Drawing Sheets

RHEOMETER FOR DETERMINING EXTENSIONAL ELASTICITY

The present invention relates to a method and apparatus for determining the resistance to extensional motion of a fluid. When fluids are caused to flow, such as when they are discharged from a closed container, they exhibit a resistance to such flow. The resistance to flow may be attributed in part to the shear viscosity of the fluid, i.e. the resistance to relative motion between adjacent layers of the fluid, and in part to the extensional resistance, i.e. the resistance to stretching motion resulting from the change in velocity of the fluid in the flow direction.

Simple fluids or Newtonian fluids such as water, oils, alcohols and hydrocarbons in general exhibit a fluid property, commonly referred to as shear viscosity or viscosity, that is independent of the rate of shearing motion. As a consequence, the performance of Newtonian fluids under various flow conditions is reasonably predictable.

More complex fluids or non-Newtonian fluids such as solutions of long-chain polymers generally do not exhibit a constant shear viscosity over a range of shear rates. The viscosity of these fluids is dependent upon the rate of shear. Many non-Newtonian fluids also exhibit a resistance to stretching motion, referred to below as extensional elasticity, and it is becoming more important to be able to quantify the degree of such extensional elasticity of these fluids. Moreover, certain fluids may appear Newtonian when their shear viscosity is measured, i.e. show a constant shear viscosity, but in fact, due to this extensional resistance, they exhibit non Newtonian characteristics when in use. Their actual performance and their predicted performance based on a constant shear viscosity may therefore differ significantly.

This extensional elasticity can be beneficial when present in some fluids or detrimental when present in others. For example, it may be beneficial for inks to exhibit some degree of extensional elasticity so that, upon their application to paper during the printing process, the ink will exhibit a high resistance to flow and so will not be pushed into the pores of the paper by the press. Similarly, fluids used to expel oil from oil bearing strata ("pusher fluids") should have a high resistance to flow. As pusher fluids pass through the strata, they travel through pores of constantly varying cross sectional area. Therefore, a fluid having a high extensional elasticity, i.e. a resistance to changes in velocity, will exhibit the required high resistance to flow, apart from the resistance contributed by shear viscosity.

On the other hand, the extensional elasticity may be undesirable or detrimental in some cases. For example, a paint is generally non Newtonian and should be constituted as an inelastic fluid to reduce the likelihood of filament formation and ensure that the fluid tends to spread or disperse evenly and without droplets. However, if the paint has a high extensional elasticity, filaments will tend to form as the application roller leaves the surface and will tend to break up and lead to drops of paint.

The quantification of the extensional elasticity of a fluid is therefore important to ensure that the properties of a fluid are correctly characterized and that a suitable fluid is used for a particular application.

Although there are devices currently available that purport to measure or indicate extensional elasticity, they have not been entirely satisfactory due to their cost and their difficulty of operation.

It is therefore an object of the present invention to provide a method and apparatus that permits the determination of the extensional elasticity of a fluid.

The present invention is based on the recognition that a liquid's extensional elasticity will only affect its flow characteristics when the fluid body is subjected to a flow acceleration. However, it is difficult to create a flow field which subjects the fluid only to acceleration and not simultaneously to shear. Accordingly, by comparing the characteristics of the liquid when in a flow field having only steady shear forces applied to it (i.e. no flow acceleration) with its characteristics when in a flow field subjected to acceleration and shear, an indication of the extensional elasticity of the fluid may be obtained and, if necessary, quantified.

Embodiments of the invention will now be described by way of example only with reference to the accompanying drawings, in which FIG. 1 is a schematic representation of a first apparatus used in the determination of the extensional elasticity of a fluid;

Figure 1:
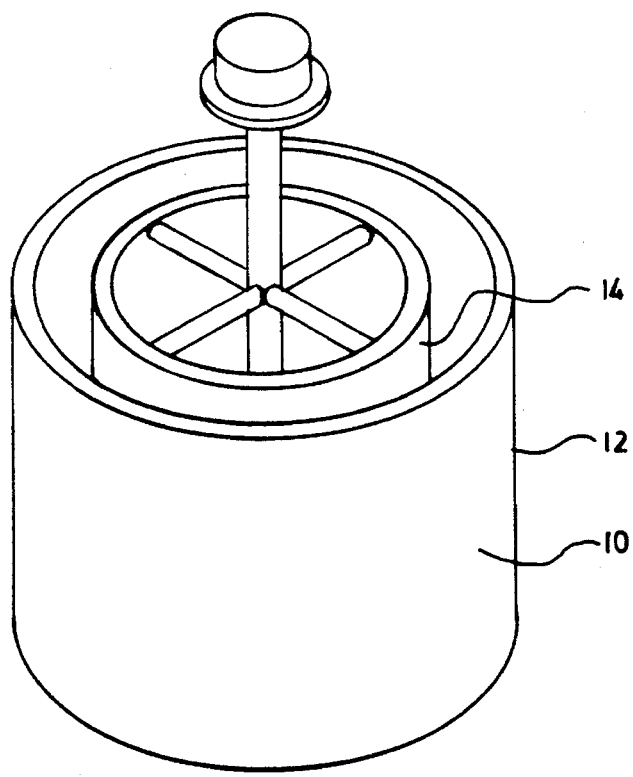

Referring therefore to FIG. 1, a viscometer 10 of known construction comprises an outer cylindrical vessel 12 to hold a fluid under test and a concentric roller 14 rotatable within the vessel 12 by a motor 16. Such a viscometer is available from Brookfield Laboratories Inc. of Stoughton, Mass. under the trade name/model number Brookfield Viscometer. Rotation of the roller 14 within the vessel 12 establishes a flow field where the shear rate of the fluid is substantially uniform. The rotational speed of the roller 14 and the torque required from the motor 16 to rotate the roller 14 are measured and from these measurements the shear viscosity of the fluid under test can be determined. The shear viscosity can be determined at a number of shear rates by varying the rotational speed of the roller 14 while maintaining the temperature of the fluid constant and noting the torque applied by the motor 16. Alternatively, the torque transferred through the fluid to the outer cylinder 12 may be measured. In both cases, data of shear viscosity versus shear rate can be obtained.

For a Newtonian fluid or one exhibiting Newtonian characteristics, the viscosity will not vary with the shear rate. However, for non-Newtonian fluids, the viscosity may vary with changes in the shear rate, although as noted above some non-Newtonian fluids do exhibit a constant viscosity when tested in a flow field having a uniform shear rate.

Figure 2:
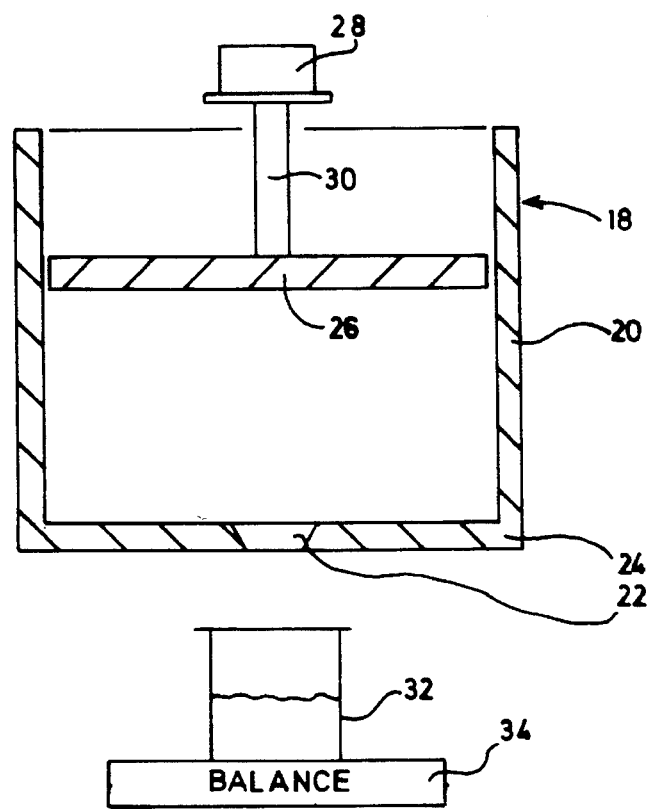
FIG. 2 is a sectional view of a second apparatus used in the determination of the extensional elasticity of the fluid.

The characteristics of the fluid are then determined using a rheometer 18 shown in FIG. 2. The rheometer 18 consists of a cylindrical wall 20 and a base 24. The wall 20 has an inner circumferential surface 21 and base 24 is provided with an aperture 22. The aperture 22 is shown as frustoconical in section although other sections can be used, such as smoothly curved. It is, however, preferred that the aperture 22 has a progressively decreasing cross-section to maximize the contribution of extensional elasticity to the flow resistance. The aperture must ensure that the fluid in the body is caused to accelerate as it passes through the aperture in order to measure the extensional elasticity. In a preferred embodiment, aperture 22 had a minimum diameter of 1 mm a cone angle of 90° and the inner diameter of the wall 20 was 30 mm.

A piston 26 is located within the cylindrical wall 20. The piston 26 has a clearance relative to the surface 21 sufficient to ensure that fluid does not pass between the piston and the sidewalls but at the same time does not introduce significant shear forces on the piston to retard its vertical motion. Piston 26 supports a known mass 28 on a piston rod 30 to produce a constant vertical force on the piston 26.

Fluid flowing through the aperture 22 is collected in a receptacle 32 which is supported on a balance 34.

In use, the test fluid is inserted into the cylinder 20 and the piston 26 is located within the cylinder to enclose the body of fluid. The force from mass 28 is applied to the piston rod 30 and the fluid is allowed to flow through the aperture 22 into the receptacle 32. The fluid is maintained at the same constant temperature as in the first apparatus. The mass of fluid flowing in a predetermined time is measured by the scale 34 from which the flow rate may be determined.

The measurement is then repeated with different masses 28 to produce varying forces on the piston 26. For each measurement, the mass of fluid in a given time flowing through the aperture 22 is measured.

The results obtained from the rheometer 18 are then plotted as a function of a parameter indicative of force versus a parameter indicative of flow rate to obtain a set of indicated values that include the effects of both the shear viscosity and the extensional elasticity.

The area A of the piston 26 and the minimum diameter D of the aperture 22 are constant throughout the tests and may be accurately determined for each apparatus 18. From the mass flow rate of the fluid as measured by the receptacle 32 and from the area of the aperture 22, the average velocity (U) of fluid flowing through the aperture 22 at its minimum cross section can be computed for each of the applied forces 28.

Figure 3:
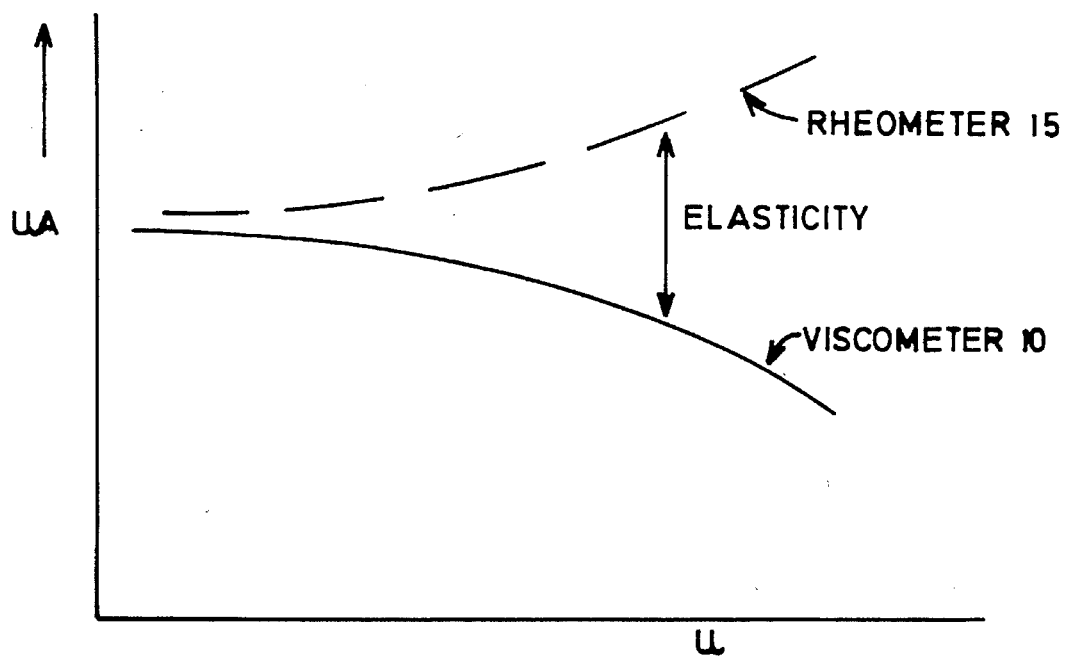
FIG. 3 is a curve showing a comparison of the results obtained from the first and second apparatuses shown in FIGS. 1 and 2 respectively.

As shown in FIG. 3, the characteristics of the fluid obtained from the rheometer 18 are conveniently plotted as a curve of $$\frac{FD}{UA} \text{ versus } \frac{U}{D},$$

, where

F is the force produced by mass 28;

D is the diameter of the aperture 22;

U is the average velocity of the fluid expelled through the aperture 22 by the force F; and A is the cross-section area of the piston 26.

The parameter $$\frac{FD}{UA}$$

is indicative of applied force and conveniently has units of viscosity. Similarly, the parameter $$\frac{U}{D}$$

is indicative of flow rate.

The curve obtained from the rheometer 18 is shown as the chain-dot line in FIG. 3.

From the results obtained from the viscometer 10 shown in FIG. 1, it is possible to compute an equivalent curve that theoretically would be obtained from the fluid if it did not exhibit extensional elasticity. Thus, given the variation of the viscosity with the shear rate obtained from the apparatus of FIG. 1, it is possible to compute the velocity through the aperture 22 in the apparatus of FIG. 2 that would be obtained with a given applied force. The velocity through this aperture is predicted using one of a number of commercially available computer programs for modelling flow, such as that known as Polyflow and available from Professor M. J. Crochet, Place de l'Université 16, B-1348 Louvain-La-Neuve, Belgium.

The computer results are generated using the values of shear viscosity obtained from the apparatus of FIG. 1 so that these results indicate the flow characteristics without the effect of extensional elasticity. These computed results are used to generate a set of reference values which can then be plotted on the curve of FIG. 3 as shown by the solid line. A comparison between the set of reference values obtained from the measurements made with the apparatus of FIG. 1 and the set of indicated values obtained from the apparatus of FIG. 2 can thus be made and the difference between the two curves is an indication of the extensional elasticity of the fluid.

With the apparatus of FIG. 1, the steady shear rate in the fluid field does not subject the body of fluid to acceleration and therefore the measurements obtained are not influenced by the extensional elasticity of the fluid. The results are an indication of the shear viscosity alone.

With the apparatus shown in FIG. 2, however, passing the fluid through the orifice 22 subjects it to an acceleration so that the effects of the extensional elasticity of the fluid and the shear viscosity of the fluid contribute to the overall measurements. By computation, the flow through the apparatus of FIG. 2 for a fluid having the characteristics obtained from the apparatus of FIG. 1 may be predicted, the difference between the computed results and the observed results is attributable solely to the extensional elasticity of the fluid. A comparison between the two, therefore, provides an indication of extensional elasticity.

The use of computer modelling to predict the flow through aperture 22 of a fluid having the same shear viscosity characteristics as the fluid under test but zero extensional elasticity is applicable to all fluids and flow rates. However, in certain special cases where the shear viscosity is constant, the set of reference values based on the data from the viscometer 10 can be computed from results obtained with an equivalent Newtonian fluid from the rheometer 18. In practical terms however the computer modelling is believed to be preferable and the alternative analytical techniques will not be described further.

Figure 4:
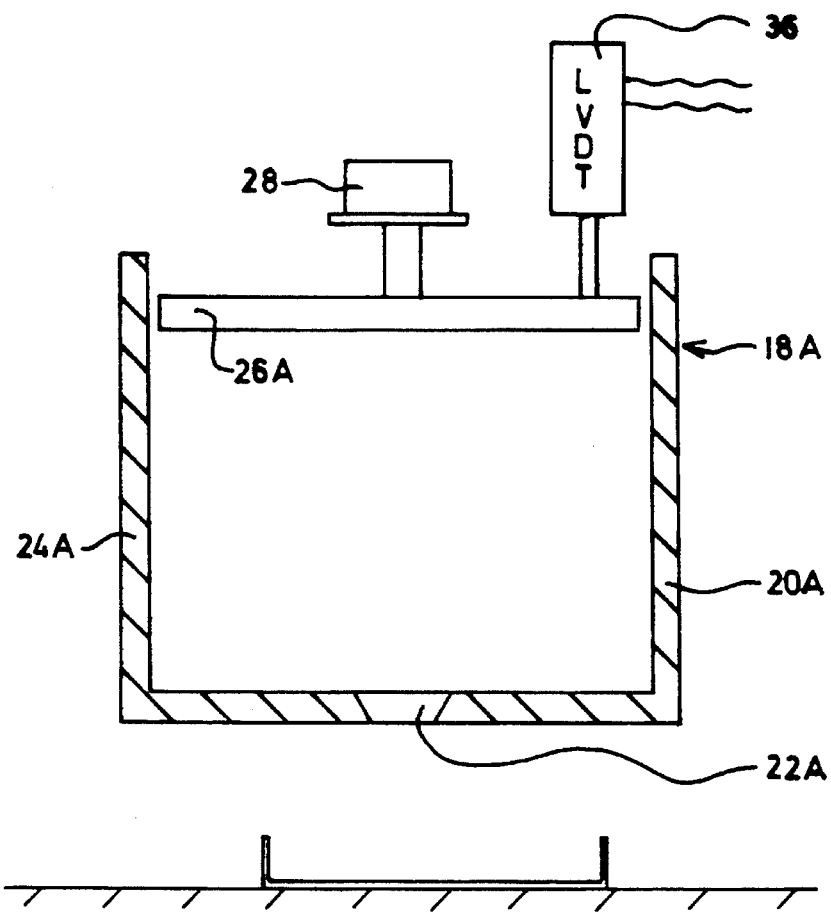
FIG. 4 is a sectional view similar to FIG. 2 of an alternative embodiment of apparatus.

The rheometer 18 may be modified in a number of ways to facilitate the measurement of extensional elasticity. As shown in FIG. 4, in which like components will be identified with a like reference numeral with the suffix "a" added for clarity, the piston 26a is monitored by a linear voltage displacement transducer (LVDT) 36 which provides an instantaneous indication of the position and rate of movement of the piston 26a. The rate of movement of the piston 26a indicates the mass flow rate of fluid being expelled from the cylinder 20a through the aperture 22a and from this the velocity of the fluid in the aperture 22a may be calculated. Accordingly, it is not necessary to utilize the balance 34.

The apparatuses of FIGS. 2 and 4 may also be modified by providing a motor and load cell to exert a constant force over the passage of the piston 26 or to vary the force during the passage of the piston so that a single expulsion of fluid from the rheometer 18 may be used to obtain results in respect of a number of applied forces.

As a further alternative, the rheometer may be formed as a vessel closed at the base 24 and an aperture 22 formed in the piston 26. In this case, the fluid is expelled from one side of the piston to the other and the mass flow rate is measured by observing the rate of movement of the piston 26. Similarly, the aperture 22 may be formed as a number of individual apertures in either the base or piston.

An indication of the extensional elasticity of the fluid may be obtained from plots different to those shown in FIG. 3 and in some cases it may be necessary to obtain an indication of extensional elasticity only under a particular condition rather than a range of conditions. In such a case, the indication of extensional elasticity may be obtained by comparing the measurements obtained in a field subjected only to shear forces and the measurements obtained in a field subjected to shear and acceleration forces for that condition only rather than over a range of conditions.

We claim:

1. A method of determining the extensional elasticity of a fluid comprising the steps of (i) determining in a first apparatus a set of reference values indicative of the shear viscosity of said fluid by performing measurements in said first apparatus in a flow field where the shear rate of the fluid is substantially uniform, (ii) determining in a second apparatus a set of indicated values representative of the shear viscosity and extensional elasticity of the fluid by performing measurements in said second apparatus in a flow field where a portion of the body of fluid under test is accelerated by application of a known force, (iii) computing a set of theoretical values for the second apparatus from the set of values determined in the first apparatus assuming the fluid has no extensional elasticity, and (iv) comparing a value from the set of values obtained from the second apparatus with a corresponding value from the set of theoretical values computed from the first apparatus to obtain an indication of the extensional elasticity of the fluid.

2. A method according to claim 1 wherein said fluid is accelerated in said second apparatus by expelling fluid from an enclosed volume through an aperture.

3. A method according to claim 2 wherein said measurements performed during acceleration of said fluid include determining the flow rate of fluid passing through said aperture.

4. A method according to claim 3 wherein each of said indicated values obtained in said second apparatus is represented as a comparison between a parameter indicative of the flow rate of fluid flow through said aperture and a parameter indicative of the ratio of the force producing the flow and the resultant flow rate through said aperture.

5. (amended) A method according to claim 2 wherein said set of reference values is determined by operating said first apparatus at a plurality of shear rates and said set of indicated values is determined by operating said second apparatus at a plurality of forces to permit comparison of said values over a range of conditions.

6. A method according to claim 1 wherein each of said set of theoretical values and said set of indicated values is expressed as $$\frac{FD}{UA} \text{ versus } \frac{U}{D}$$

where

F is the force exerted on said fluid;

D is the diameter of the aperture through which fluid passes;

U is the velocity of fluid passing through the aperture; and

A is the area over which the force W is applied;

and differences between said values of $$\frac{FD}{UA}$$

for a given values of $$\frac{U}{D}$$

is an indication of the extensional elasticity of the fluid.

* * * * *